(12) United States Patent
Schafer et al.

(10) Patent No.: US 12,201,856 B2
(45) Date of Patent: Jan. 21, 2025

(54) STRUCTURES AND METHODS FOR MODIFYING ULTRASOUND TREATMENT

(71) Applicant: BrainSonix Corporation, Sherman Oaks, CA (US)

(72) Inventors: Samantha F. Schafer, Ambler, PA (US); Mark E. Schafer, Ambler, PA (US)

(73) Assignee: BrainSonix Corporation, Sherman Oaks, CA (US)

( * ) Notice: Subject to any disclaimer, the term of this patent is extended or adjusted under 35 U.S.C. 154(b) by 121 days.

(21) Appl. No.: 17/680,466

(22) Filed: Feb. 25, 2022

(65) Prior Publication Data

US 2022/0331612 A1    Oct. 20, 2022

Related U.S. Application Data

(60) Provisional application No. 63/177,084, filed on Apr. 20, 2021.

(51) Int. Cl.
*A61B 8/00* (2006.01)
*A61N 7/00* (2006.01)

(52) U.S. Cl.
CPC .............. *A61N 7/00* (2013.01); *A61B 8/4281* (2013.01); *A61N 2007/0021* (2013.01); *A61N 2007/0056* (2013.01)

(58) Field of Classification Search
CPC .... A61N 2007/0021; A61N 2007/0026; A61N 7/00; A61B 8/4281
See application file for complete search history.

(56) References Cited

U.S. PATENT DOCUMENTS

| 2003/0069500 A1* | 4/2003 | Bullis | A61B 8/4281 |
| | | | 600/442 |
| 2004/0218727 A1* | 11/2004 | Shoenfeld | A61B 6/0414 |
| | | | 378/167 |
| 2005/0095296 A1* | 5/2005 | Lowman | G10K 11/02 |
| | | | 600/437 |
| 2006/0184070 A1 | 8/2006 | Hansmann et al. | |
| 2007/0142717 A1* | 6/2007 | Lowery | A61B 5/14552 |
| | | | 600/323 |

(Continued)

FOREIGN PATENT DOCUMENTS

| KR | 101751755 B1 | 6/2017 |
| WO | 2014127235 A1 | 8/2014 |

OTHER PUBLICATIONS

European Patent Office, International Search Report and Written Opinion issued in International Patent Application No. PCT/US2022/017811 on Jun. 3, 2022, 19 pages.

(Continued)

*Primary Examiner* — Amelie R Davis
(74) *Attorney, Agent, or Firm* — Thompson Hine LLP

(57) ABSTRACT

Structures and methods for ultrasound treatment of neurological and psychological conditions, using energy levels which do not cause heating or cavitation. The structure includes an outer casing comprising a first material, and a disk positioned inside the outer casing. The disk comprises a second material that differs in composition from the first material and that has a higher acoustic attenuation of ultrasound energy than the first material.

18 Claims, 9 Drawing Sheets

(56) References Cited

U.S. PATENT DOCUMENTS

| | | | |
|---|---|---|---|
| 2011/0071079 A1* | 3/2011 | Ameer | A61K 38/38 514/15.3 |
| 2013/0144193 A1* | 6/2013 | Lewis, Jr. | A61B 8/4281 601/2 |
| 2014/0235725 A1 | 8/2014 | Morgan | |
| 2019/0150892 A1* | 5/2019 | Arant | A61M 35/006 |
| 2019/0321122 A1* | 10/2019 | Hewes | A61N 7/00 |
| 2020/0138580 A1* | 5/2020 | Carpentier | A61N 7/00 |
| 2020/0155872 A1 | 5/2020 | Chen et al. | |
| 2021/0361975 A1 | 11/2021 | Schafer et al. | |
| 2022/0296214 A1* | 9/2022 | Zheng | A61B 8/4281 |

OTHER PUBLICATIONS

The International Bureau of WIPO, International Preliminary Report on Patentability and Written Opinion issued in International Patent Application No. PCT/US2022/017811 on Oct. 24, 2023, 9 pages.

M. E. Schafer, N. M. Spivak, A. S. Korb and A. Bystritsky, "Design, Development, and Operation of a Low-Intensity Focused Ultrasound Pulsation (LIFUP) System for Clinical Use," in IEEE Transactions on Ultrasonics, Ferroelectrics, and Frequency Control, vol. 68, No. 1, pp. 54-64, doi: 10.1109/TUFFC.2020.3006781 (Jan. 2021).

\* cited by examiner

STRUCTURES AND METHODS FOR MODIFYING ULTRASOUND TREATMENT

CROSS-REFERENCE TO RELATED APPLICATIONS

This application claims the benefit of U.S. Provisional Application No. 63/177,084, filed Apr. 20, 2021, which is hereby incorporated by reference herein in its entirety.

TECHNICAL FIELD

The disclosure is directed to ultrasonics and, more specifically, to structures and methods for ultrasound treatment of neurological and psychological conditions using energy levels which do not cause heating or cavitation.

BACKGROUND

Ultrasonic or ultrasound treatment may be used to treat various conditions, such as neurological and psychological conditions. During treatment, a certain level of ultrasound energy should be delivered to a specific area in the brain, for example but not limited to, the amygdala, the hippocampus, the entorhinal cortex, the ventral striatum, and the thalamic area, among others. The ultrasound energy is delivered through the bone of the skull and focused on the desired region within the skull.

When doing research, the patient/subject should be unaware of the treatment condition, so that the true effects of the treatment can be assessed independently of any conscious action of the patient. This is called "blinding" of the subject. It is also known as a "placebo" or "sham" treatment, and is employed to determine the effect of an ultrasound treatment when the patient can affect the outcome by their actions, inactions, or reactions.

Some neurological conditions, such as anxiety, can be influenced by factors other than the ultrasound treatment. The ultrasound transducer itself, for instance, can generate audible sounds while delivering ultrasound for treatment. Such audible sounds can be perceived by a patient and might raise, lower, or change the patient's anxiety. An approach for not administering ultrasound treatment to the placebo test group has been to apply the transducer to the subject's head, but to not activate the transducer such that there is no actual ultrasound treatment.

The approach of not administering ultrasound to the placebo group of patients fails to adequately address the problem because of the mechanics of the transducer itself. When turned on and administering ultrasound, the transducer creates an audible clicking or buzzing sound that can be heard by the patient. If the transducer is turned off, so as to not administer ultrasound, the clicking sound is not made by the transducer and thus not heard by the patient. This creates a distinguishable difference between actual treatment and placebo treatment that can be discerned by the patient, as well as by the operator administering the treatment.

Another approach for inhibiting ultrasound treatment is to use a non-functional ultrasound transducer, but this presents similar issues with respect to the audible clicking or buzzing sound as the case of not energizing the transducer.

Another approach for inhibiting ultrasound treatment is to not properly acoustically couple the ultrasound transducer to the subject's head, either by leaving an air gap between the front of the transducer and the subject's skull or by mounting the transducer in a reversed position (facing away from the subject's skull). In either case, the difference between actual treatment and placebo treatment can be sufficient that the subject is aware that the treatment conditions are different. The operator who must place the transducer certainly is aware of the difference.

The approaches to patient blinding and/or operator blinding during single- or double-blind studies have not proven adequate, and involve electrical approaches (such as not energizing the transducer) or mechanical approaches (such as turning the transducer to face away from the patient). Both approaches are unwantedly discernable by either the patient or the operator, or both.

As a further example of blinded procedures, there may be a desire for a third condition, beyond full treatment and sham or placebo treatment. Such a third condition may involve a modification of the ultrasound beam characteristics, such as reduction or modification of exposure (but not complete elimination) which might involve a transducer transmitting surface geometry smaller than that used for a full treatment, or an annular or otherwise geometrically limited or modified transmitting surface geometry, which would lead to a different ultrasound beam pattern within the patient. No current single element transducer technology allows for such modifications, except for the case of substituting a modified transducer. While this substitution approach would be indiscernible to the patient, the operator would be aware of the substitution. It would also involve additional expense for the creation of additional transducers with the modified geometry.

Improved structures and methods for inhibiting, allowing, or modifying ultrasound treatment are need.

SUMMARY

In an embodiment of the invention, a structure includes an outer casing comprising a first material, and a disk positioned inside the outer casing. The disk comprises a second material that differs in composition from the first material and that has a higher acoustic attenuation of ultrasound energy than the first material.

In an embodiment of the invention, a method includes introducing a first layer of a first material into a mold in a first stage of a molding process, inserting a disk into the mold, and introducing a second layer of the first material into the mold in a second stage of the molding process. The disk is surrounded by a gap between the disk and the mold, and the second layer of the first material fills the gap to provide a physical connection with the first layer. The method further includes curing the first layer and the second layer of the first material.

In an embodiment of the invention, a treatment method includes transmitting ultrasound energy from an ultrasound transducer through a first pad to provide an actual exposure. The method further includes transmitting the ultrasound energy from the ultrasound transducer through a second pad that significantly attenuates transmission of the ultrasound energy to provide a placebo exposure.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION

Figure 1A:
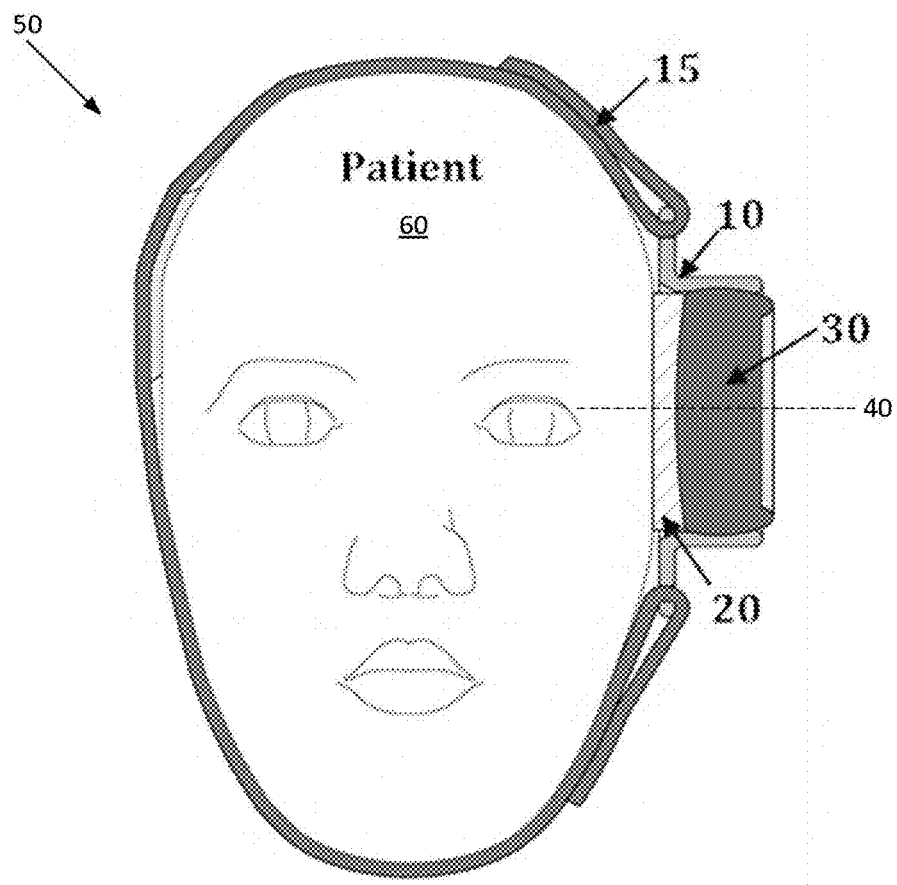
FIG. 1A schematically illustrates an ultrasonic treatment device with a transducer holder holding an ultrasonic transducer at a first angle (e.g., a 0-degree angle), with a corresponding gel pad, in accordance with various embodiments.

FIG. 1A is a schematic representation of the ultrasound apparatus 50 as applied to the patient 60. Transducer holder 10 may be affixed to patient 60's skull with elastic straps 15. Transducer 30 clips into the holder 10. Gel pad 20, a 0-degree pad, is coupled to transducer 30 and allows for the transmission of ultrasound to the patient, as ultrasound cannot travel through air. The transmission plane 40 is where the ultrasound will be focused. Transducer 30 is off and not firing pulses.

In an embodiment, the transducer 30 may be connected to a system as provided in "Design, development and operation of a Low Intensity Focused Ultrasound Pulsations (LIFUP) system for clinical use" by Schafer, Spivak, Korb, and Bystritsky, IEEE Trans Ultrason. Ferroelectr. Freq Control 68(1):54-64 2021 DOI: 10.1109/TUFFC.2020.3006781, and/or U.S. Patent Publication No. 2021/0361975, which are hereby incorporated by reference herein in their entirety.

Figure 1B:
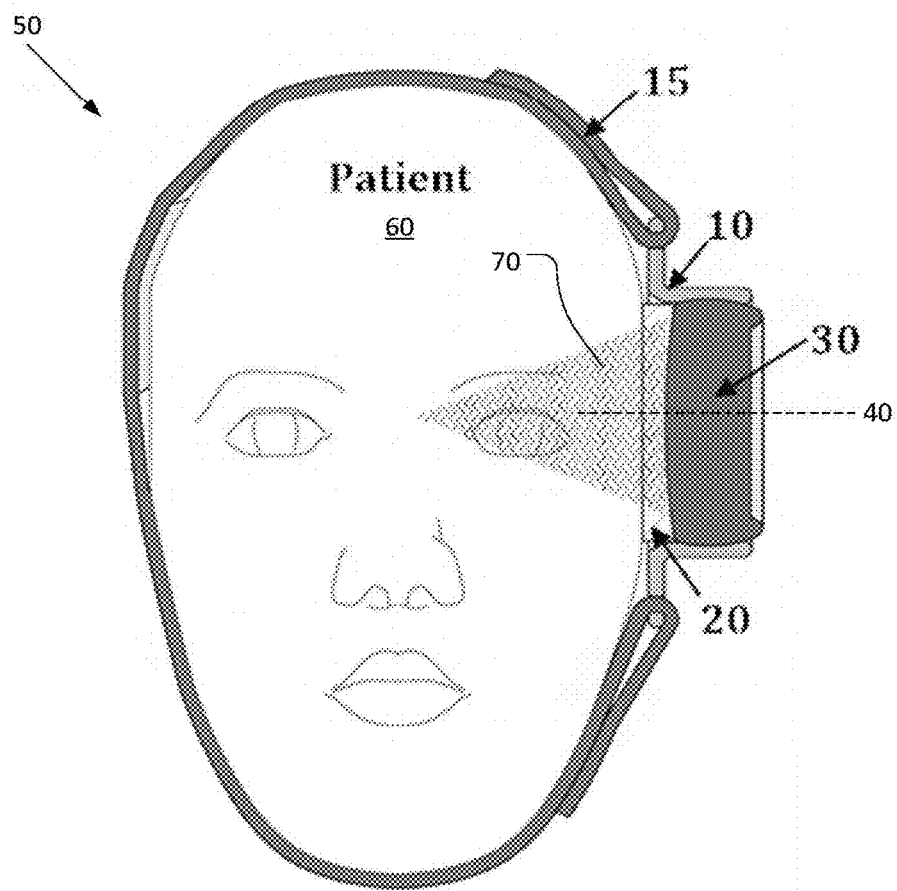
FIG. 1B illustrates the ultrasonic treatment device of FIG. 1A, showing a path of the ultrasonic beam from the transducer, through a gel pad, in accordance with various embodiments.

FIG. 1B is a schematic representation of the ultrasound apparatus 50 as described in FIG. 1A, but with transducer 30 energized to an on-state and firing pulses to form the beam 70, along transmission plane 40, in the brain of the patient 60. Gel pad 20 allows the ultrasound to be transmitted and pass through to the brain of the patient 60.

Figure 2A:
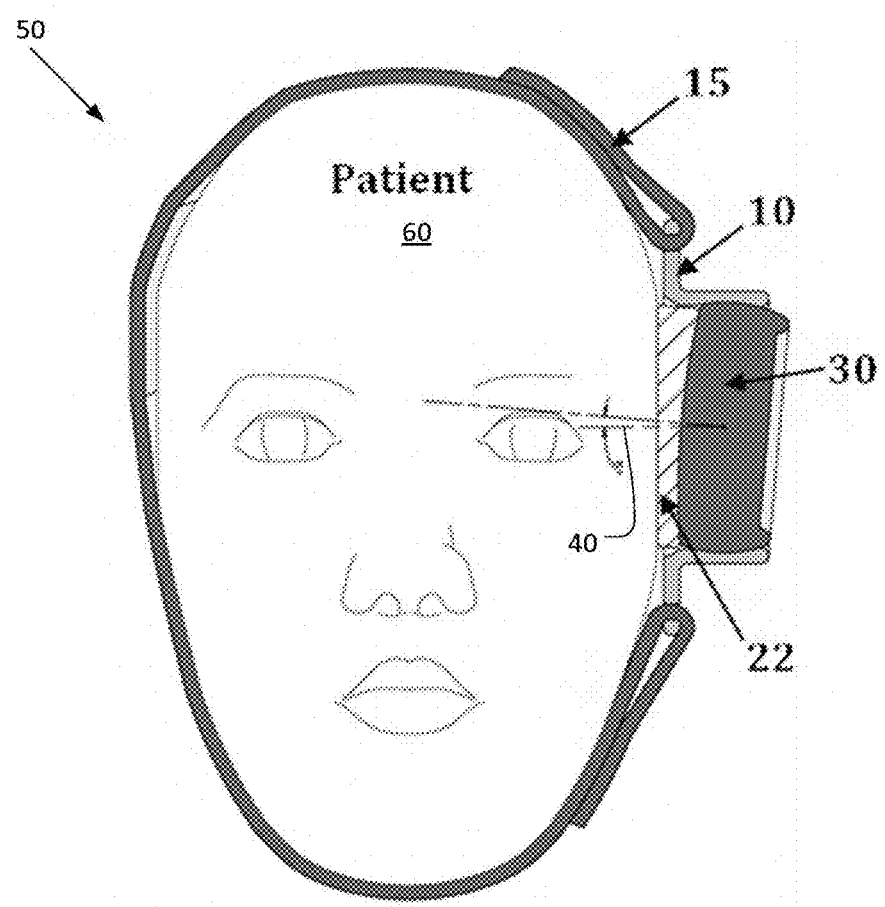
FIG. 2A illustrates an ultrasonic treatment device with a transducer holder holding an ultrasonic transducer at a second angle (e.g., a 5-degree angle), with a corresponding gel pad, in accordance with various embodiments.

FIG. 2A is a schematic representation of the ultrasound apparatus 50 as applied to the patient 60. Transducer holder 10 may be affixed to patient 60's skull with elastic straps 15. Transducer 30 clips into the holder 10. Gel pad 22, a 5-degree pad, is coupled to transducer 30 and allows for the transmission of ultrasound to the patient, as ultrasound cannot travel through air. The transmission plane 40 is where the ultrasound will be focused. Transducer 30 is off and not firing pulses.

Figure 2B:
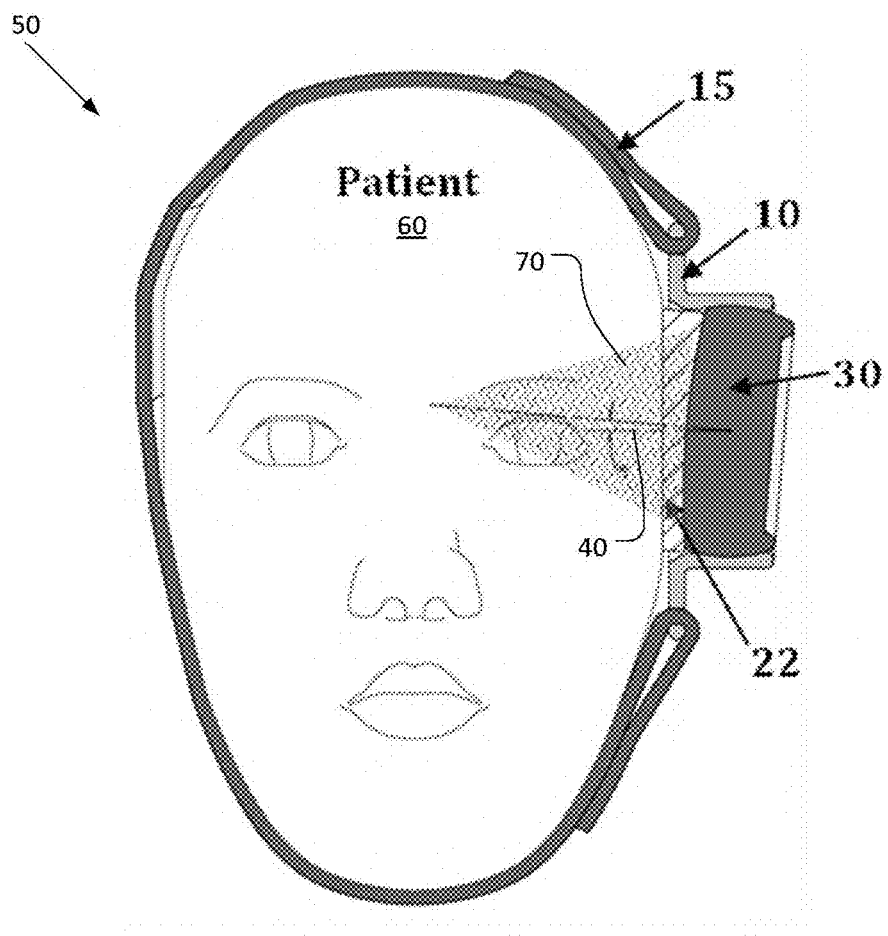
FIG. 2B illustrates the ultrasonic treatment device of FIG. 2A, showing a path of the ultrasonic beam from the transducer, through a gel pad, in accordance with various embodiments.

FIG. 2B is a schematic representation of the ultrasound apparatus 50 as described in FIG. 2A, but with transducer 30 on and firing pulses to form the beam 70, along plane 40, in the patient 60's brain. Gel pad 22 changes the trajectory of beam 70 by 5-degrees. The gel pad 22 allows the ultrasound to be transmitted and pass through to the brain of the patient 60. The gel pads 20, 22 may be employed to provide actual exposures or treatments.

Depending upon the anatomical region within the brain that is to be treated with ultrasound, the angle of the transducer 30 (provided by the wedge angle of the gel pads) may differ, and the angle is not exclusively limited to 0 degrees or 5 degrees, but can span a continual range from 0 degrees to at least 5 degrees. In an embodiment, the angle may range from 0 degrees to 5 degrees. The gel pads may be sufficiently flexible, compressible, and conformable to accommodate a range of transducer angles. For instance, a transducer plane 40 providing an angle of 0 or 1 or 2 or 3 degrees would be accommodated by a 0 degree gel pad 20, while a transducer angle 40 between 3 and 8 degrees would be accommodated by a 5 degree gel pad 22. Also, gel pads may be created with wedge angles other than just 0 and 5 degrees. Angles greater than 8 degrees may produce distortion in the ultrasound beam because of the acoustic properties of the skull.

Figure 3:
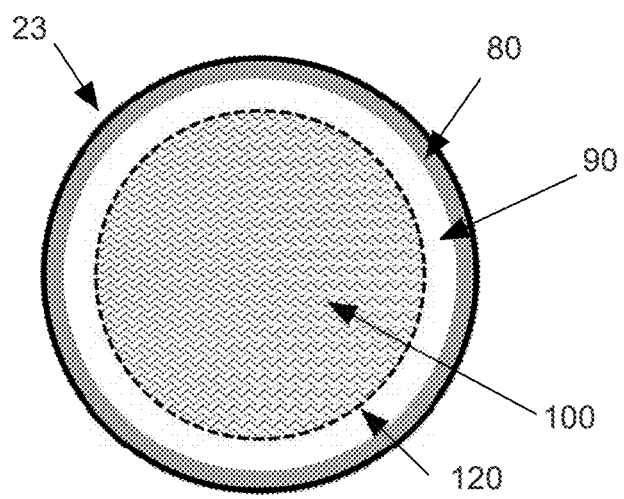
FIG. 3 is a schematic representation of the top view of a non-transmit gel pad that may be coupled to the transducer during treatment.

FIG. 3 is a schematic representation of the top view of a non-transmit gel pad 23 to be coupled to the transducer 30 described in previous figures. Mating ring 80 allows for the gel pad to mate with the face of the transducer 30. In an embodiment, the mating ring 80 may be made by additive manufacturing methods (3D printing) using fused deposition modeling (FDM)-printed Ultem 9085 (or other suitable thermoplastic resin), or can be molded using, for instance, DuPont Nylon 66-MinIon 10640 NC010 or Polyetherimide 1000 (or other similar polymer). In an embodiment, the material 90 may be a skin-safe two-part silicone with little to no ultrasonic attenuative properties (Dragon Skin NV-10, Smooth-On Inc, Macungie PA). The material 90 may be dyed white with a skin-safe silicone dye (Silc-Pig, Smooth-On Inc, Macungie PA) to hide the inner contents of the pad. Although this material provides the necessary acoustic properties and mechanical stability and flexibility, other similar materials may potentially be used. The acoustic requirements include, but are not limited to, low loss (less than 5%), and little refractive bending of the beam due to sound speed differential (therefore sound speed within 20% of tissue). Mechanically, the gel pads may conform to both the front of the transducer 30 and the surface of the skull, and must be compressible (for example, Shore 30A) so as to fill the gap in between the two. In use, fluid ultrasound coupling material, such as Aquasonic 100 (Parker Labs, New Jersey) may be placed between the transducer 30 and the gel pad, and gel pad and the skull, to permit adequate acoustic transmission.

The material 90 may be made in a process that can adapt to the inclusion of a foam disk 100. For instance, the gel pad material 90 may restrict processing temperatures (i.e., heating above, e.g., 170° C.) during a molding process that could melt the foam disk material 100. Also, the final gel pad material 90 should be optically opaque or, alternatively, highly translucent so that it is not visually apparent whether the foam disk 100 is present or not present in the final device and visualization of the foam disk 100 is prevented. For example, gel pads 20 made from materials that are completely clear would permit easy identification of gel pads that contained a foam disk 100.

The foam disk 100 may be imbedded into material 90 during a multi-stage curing process as to prevent any portion of the foam from floating to the surface of the material during curing. The foam disk 100 is comprised of a material with a different composition than the material 90 and that has a higher acoustic attenuation of ultrasound energy than the material 90. In an embodiment, the foam disk 100 may comprised of an open cell material, such as an open cell polyethylene foam wrap material (e.g., McMaster Carr, Elmhurst IL, PN 2007T41). In an alternative embodiment, the foam disk 100 may be comprised of a closed-cell material (e.g., Styrofoam). Open cell foam may lend better adherence to material 90, and result in a better cohesion within the final product. Closed cell foam may also tend to be stiffer and more brittle than thin open cell foam, which may affect the mechanical performance and may also make the non-transmit pads more differentiable from the transmit pads. The thickness of material 100 should be as thin as possible, for instance ⅟₃₂ inch, because it should fit within the existing structure of the gel pads. If thicker gel pads are designed for the transmitting case, then this permits thicker foam disks 100 to be used, although typically the gel pads are designed to be as thin as possible. Degassing during the assembly process may not be necessary when making non-transmit pads because any residual air bubbles within the material after curing will add to the ultrasound blocking effect of the pad.

Figure 4A:
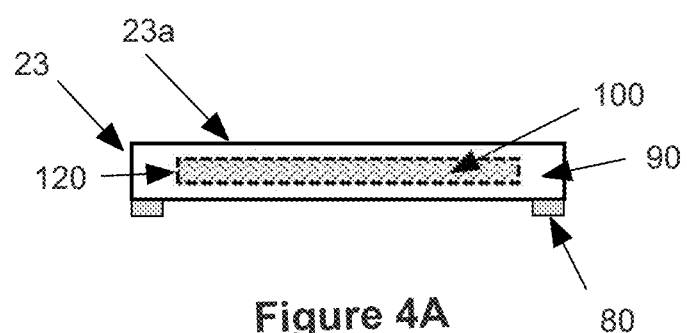
FIGS. 4A, 4B are schematic representations of the side cross-sectional view of the non-transmit gel pads (0-degree and 5-degree) that may be coupled to the transducer during treatment.
Figure 4B:
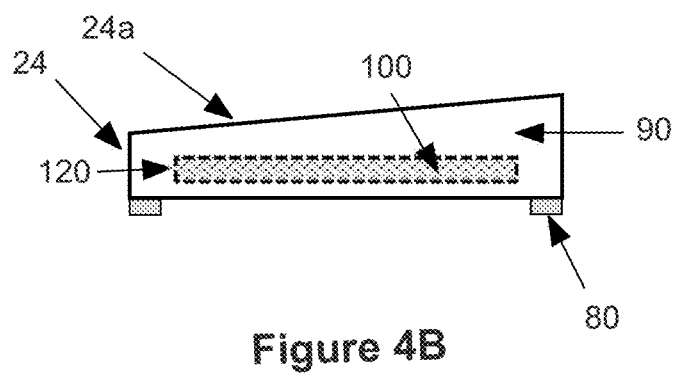

FIGS. 4A, 4B are schematic representations showing side cross-sectional views of each of the non-transmit 0-degree pads 23 and 5-degree 24 pads, respectively. The foam disk 100 is imbedded in the material 90 during production such that the material 90 provides an outer casing that surrounds the imbedded foam disk 100. In an embodiment, the foam disk 100 may be centrally imbedded into the middle of the material 90. In an embodiment, a thickness of the material 90 may be present in a gap between the foam disk 100 and the respective exterior surfaces 23a, 24a of the pads 23, 24. That is, the foam disk 100 has an outer boundary or edge that is smaller than the inner extent of the mold, such that a gap exists between the foam disk 100 and the mold about the outer edge of the foam disk 100. The gel pads 23, 24 may be employed to provide placebo exposures or treatments.

Figure 5:
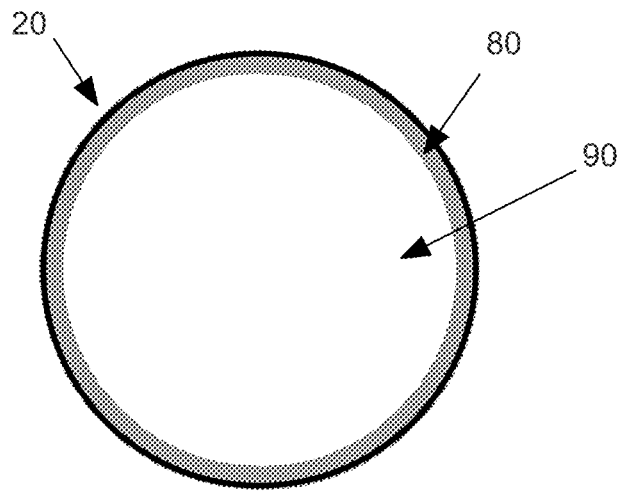
FIG. 5 is a schematic representation of the top view of a transmit gel pad that may be coupled to the transducer during treatment.

FIG. 5 is a schematic representation showing a top view of a transmit gel pad 20 coupled to the transducer 30 as described in previous figures. Mating ring 80 allows for the gel pad 20 to align with the face of the transducer 30. Transducer 30 may have an outer ridge on its face that the mating ring 80 fits within the outer ridge. This aligns the gel pad 20 on the face of transducer 30. The size of the gel pad 20 should therefore match the transducer 30. Transducer 30 may have any diameter, but clinically useful transducers range, for instance between 20 mm and 70 mm, with 60 mm being common. In use, fluid ultrasound coupling material, such as Aquasonic 100 (Parker Labs, New Jersey) may be applied to the gel pad 20 and the face of the transducer 30, the gel pad 20 tends to remain in place on the transducer 30, facilitating the placement of the transducer 30 on the skull.

The face of transducer 30 may be flat, concave, or convex. The illustrations of typical transducers 30 shown in the figures depict a convex surface. The gel pads 20, 23, or 25 may have a matching concave surface such that there will be intimate physical contact between the gel pad 20, 23, or 25 and the face of the transducer 30. The opposite side of the gel pads 20, 23, or 25 may be planar, to match the surface of the skull. However, that surface may be convex if that provides a better match to the surface of the skull, depending upon the region of the head where the transducer 30 will be used. For instance, if the transducer 30 is to be placed on the top of the skull rather than the temporal region (which is generally flat) then the gel pad 20, 23, or 25 can be shaped to match the curvature of the skull surface.

While this embodiment has been directed to application of ultrasound to the skull, it is also appropriate for ultrasound application to any part of the body where experimentation methods require similar blinding of the patient and/or operator, for example in stimulation of the peripheral nervous system. In those cases, the gel pads 20 or 23 can be adapted to the surface of the skin over the area to be treated.

While the transducer 30 and gel pads 20, 23, and 25 are shown with a circular geometry, other transducer designs which may have, e.g., oval, rectangular, square or other face geometry can used. In those cases, the gel pads 20, 23, and 25 can be readily adapted by changing the molds into which the material 90 is poured, as well as changing the foam disk 100 and the mating ring 80.

The transmit pads should lack any or substantially any attenuating contents; thus, no foam disk is imbedded. Degassing may be needed prior to pot life expiration of the material 90, because any residual air bubbles within material 90 block ultrasound transmission.

After mixing part A and part B of the silicone material with the pigment, per manufacturer's instructions, the mixture may be degassed for 3 minutes at −90 kPa, then introduced into a mold by pouring during a molding process, at which time it may be degassed again for 10 minutes at the same vacuum level. A small vacuum chamber (for example, Vacuum Chamber System #752951 Carolina Supply) is sufficient, with a standard small vacuum pump.

Figure 6A:
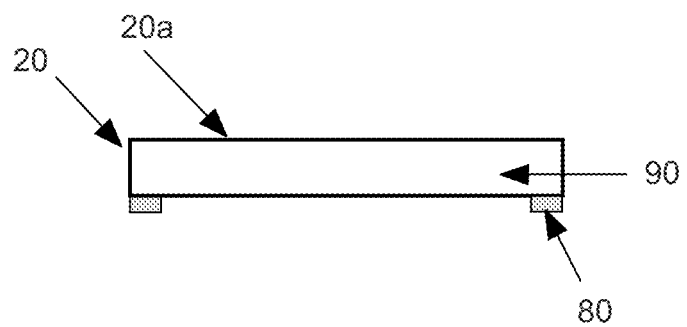
FIGS. 6A, 6B are schematic representations of the side cross-sectional view of the transmit gel pads (0-degree and 5-degree) that may be coupled to the transducer during treatment.
Figure 6B:
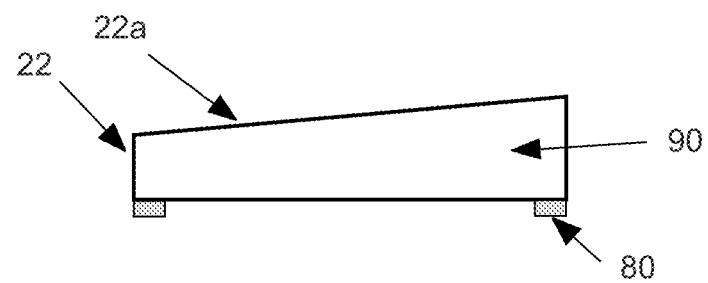

FIGS. 6A, 6B are schematic representations of the side cross-section of each of the transmit 0-degree 20 and 5-degree 22 pads, respectively. No foam disk is imbedded into these pads and the material 90 may be degassed to remove any air bubbles that might cause attenuation.

With renewed reference to FIGS. 3-4, the foam disk 100 may be centered within gel pad 23, and may be of sufficient diameter to intercept the ultrasound beam 70. Depending upon the geometry of the ultrasound beam 70, foam disk 100 may not need to completely extend over the entire area of gel pad 23, as shown in the figures. However, the relative diameter of the foam disk 100 and the gel pad 23 shown in the figures is only for purposes of clarity of illustration, and are not to be interpreted as a specific design feature. After a bottom layer of the material 90 in introduced (i.e., poured) into the mold during the molding process, the foam disk 10 is placed into the mold. While making the foam disk 100 of the same diameter as the gel pad 23 may appear to most completely block ultrasound beam 70, it is necessary that there be some region (e.g., annular region) around foam disk 100 (visible in FIGS. 3, 4A, and 4B) such that when the top layer of material 90 is introduced (i.e., poured) on top of the foam disk 100, there is physical connectivity between the top and bottom layers. Otherwise, the gel pad 23 may lack sufficient structural integrity, and could peel apart. Additionally, if the foam disk 100 is too wide, discernable features may appear on the external surfaces of the gel pad 23, defeating the purpose of having visually and physically identical transmit and non-transmit gel pads.

Figure 7A:
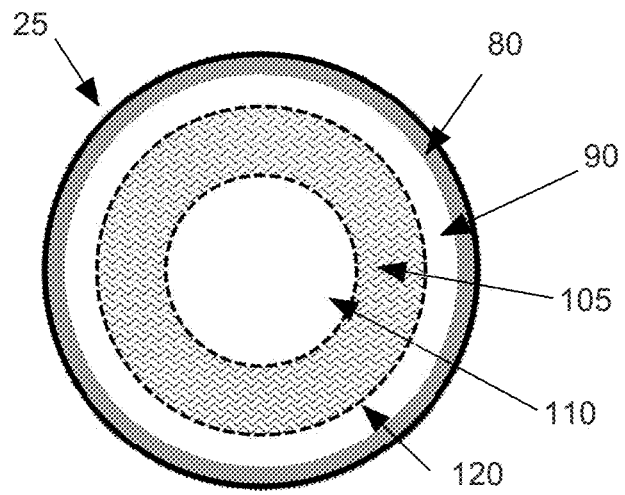
FIGS. 7A, 7B are schematic representations of the top view of modified transmit gel pads that may be coupled to the transducer during treatment.
Figure 7B:
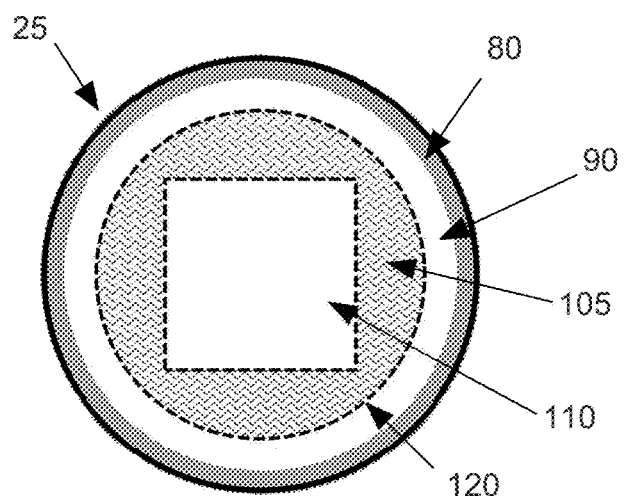
Figure 8:
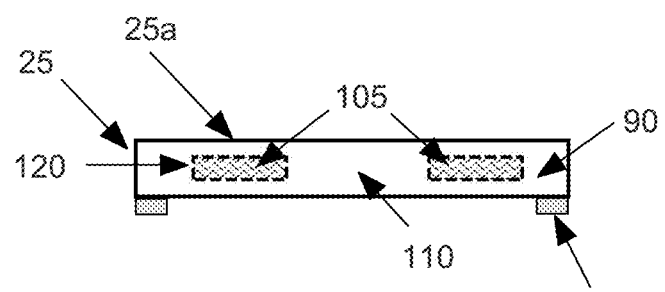
FIG. 8 is a schematic representation of the side cross-sectional view of a modified transmit gel pad.

FIGS. 7A, 7B, 8 show embodiments of a foam disk 105 that has been modified to have a central aperture 110 which allows ultrasound energy to pass through. This would have the effect of modifying the ultrasound beam, effectively changing the diameter of the ultrasound transducer. In this case, the focal depth of the transmitted ultrasound energy 70 would not change, but the beam width at the focus would increase. In an alternative embodiment, the modified foam disk 105 may lack a central aperture 110, but instead may have a smaller diameter than foam disk 100. In this case, the ultrasound beam 70 would be similar to that of an annular ultrasound element, which again would have a similar focal distance, but would be modified in its beam pattern. In an embodiment, the foam disk 105 may have a diameter that is less than 80% of the diameter of a pad that provides substantially full attenuation and non-transmission. In an embodiment, the foam disk 105 may have a diameter that is less than 85% of the diameter of a pad that provides substantially full attenuation and non-transmission. In an embodiment, the foam disk 105 may have a diameter that is less than 90% of the diameter of a pad that provides substantially full attenuation and non-transmission. In an embodiment, the foam disk 105 may have a diameter that is less than 95% of the diameter of a pad that provides substantially full attenuation and non-transmission. In an embodiment, a gel pad with the foam disk 100 may attenuate the ultrasound beam to create a loss such that less than about 0.7% of the ultrasound energy is passed, whereas a gel pad with the reduced-diameter foam disk 105 may permit a high throughput, such as 3% or more, of the ultrasound energy.

The aperture 110 may be of any shape that might be of interest beyond a circular shape, for instance an oval (when the overall transducer 30 has a circular transmitting surface geometry) or a rectangle (when the overall transducer 30 has a rectangular transmitting surface geometry), or any of a number of other non-circular shapes, such as square, star, etc. The modified foam disk 105 may also be used in angled gel pads such as that illustrated in FIG. 4B, element 24.

The disclosed embodiments allow the transducer 30 to be energized and pulsing, while effectively blocking all or substantially all ultrasound energy 70 from entering the patient's brain, or modifying the ultrasound energy 70 to provide a different ultrasound exposure pattern within the brain. In an embodiment, the gel pads 23, 24 may attenuate the ultrasound energy emitted from the transducer 30, due the positioning of the foam disk 100 in the transmission path, to less than 0.3% transmission. In an embodiment, the gel pads 23, 24 may attenuate the ultrasound energy emitted from the transducer 30, due the positioning of the foam disk 100 in the transmission path, to 0.3% and 0.7% transmission, or between −43 dB and −50 dB.

The disclosed embodiments allow for an experiment where the operator is blinded to the exposure condition, specifically in those situations where the object being exposed (e.g., a tissue sample, an animal, a cell culture) may not necessarily need to be blinded.

In contrast, previous solutions have revolved around the source of the ultrasound, the transducer 30, and not creating something that would block or modify the ultrasound energy 70.

The gel pads of the various embodiments isolate the non-ultrasound (i.e. audible) effects from the combination of the ultrasound and non-ultrasound effects. As a result, ultrasound can be selectively transmitted into the patient, without diminishing or changing the audible sound produced by the transducer. This therefore may isolate any patient reaction to the audible sound from their reaction to the ultrasound treatment, providing a way to delineate the effect of the ultrasound. The patient/subject should be blinded as to whether the ultrasound was actually transmitted into their brain, or whether the ultrasound was of different beam characteristics, without affecting the other possible cues, such as the sound. Patient blinding may be utilized in studies in which the effects with and without ultrasound energy, or of two or more ultrasound beam characteristics, are compared using the same patients or patient groups. Because the gel pads of the various embodiments block, or otherwise significantly limit, the patient/subject from differentiating between treatment conditions, the study results may not be affected. Further, when conducting such experiments, the gel pads of the various embodiments may prevent the operator applying the ultrasound transducer from having obvious cues as to the treatment condition (i.e., transmit or non-transmit). This additional aspect is known as "double-blinding", so that the operator cannot provide subtle cues to the patient/subject as to which treatment condition (with or without ultrasound energy into the brain) pertains.

The gel pads of the various embodiments may create identical testing situations for single-blind and double-blind studies for neuromodulation or other ultrasound treatments so that the patient and the person administering the treatment (operator) cannot distinguish which patient group is receiving the ultrasound treatment and which are not.

Example

A prototype transmit pad and a prototype non-transmit pad, substantially identical to pads 20, 23 disclosed herein, were fabricated and tested in a water tank with a transducer and a standard hydrophone (underwater hydrophone) to measure the actual ultrasound energy emitted from the transducer. The following table shows the difference in ultrasound transmission between the transmit and non-transmit pads. The table lists the amplitude of the waveform (in peak-to-peak volts (Vpp)) received by the hydrophone under each test condition, relative to the amplitude with no pad in place (reference condition). The test was conducted with a 60 mm diameter, 80 mm focus circular disk transducer operated at 650 kHz.

| Test condition | Received Hydrophone Waveform Amplitude |
| --- | --- |
| No Pad (water only) | 2.4 Vpp |
| Transmit Pad | 2.31 Vpp |
| Non-Transmit Pad | 25 mVpp |

The results show negligible ultrasound attenuation using the transmit pad, and a loss of ~40 dB for the non-transmit pad indicating significant ultrasound attenuation.

In a follow on experiment, six sets of transmit and non-transmit pads substantially identical to pads 22, 24 disclosed herein, were fabricated and were tested in a water tank with a transducer. The following table shows relative loss of ultrasound intensity due to the gel pad when placed in front of the transducer.

| Transmit Pad | dB | Non-Transmit Pad | dB |
| --- | --- | --- | --- |
| 1 | −0.51 | 1 | −49.88 |
| 2 | −0.51 | 2 | −46.53 |
| 3 | −0.42 | 3 | −52.55 |
| 4 | −0.51 | 4 | −46.19 |
| 5 | −0.42 | 5 | −47.25 |
| 6 | −0.33 | 6 | −47.94 |

A test was conducted to determine whether an operator could distinguish the differences in the pads from visual inspection or casual physical manipulation. An operator experienced with ultrasound treatment of patients was asked to inspect and handle two gel pads, one each of the transmit type (gel pad 20) and non-transmit type (gel pad 23). The operator was unable to distinguish them by visual inspection or casual physical manipulation, as would be the case clinically.

A test was conducted to determine whether a patient could distinguish the differences in the pads based on use in a simple exposure experiment. A subject well experienced with typical ultrasound treatments to the skull (as a repeat test subject), was exposed to typical ultrasound treatment regimen, once using the transmit pad and once using the non-transmit pad. The subject was asked to discern the difference between the two. The subject was not able to distinguish any difference, either sensation or audible, between the two types.

The embodiments of the invention provide a method of single-blind and double blind-testing that would be indistinguishable to anyone not privy to study details. For example, during clinical use, two types of pads may be supplied with individual serial numbers. The serial number of each pad may be recorded as part of the test sequence. During all tests, the transducer will be on and emitting ultrasound energy, but the specific pad will either block (or substantially block) transmission, or substantially modify transmission or allow full transmission of the ultrasound to the patient. A person aware of the specific type of pad, full transmit, modified, or non-transmit, may not be a part of the clinical situation, and may reveal the type of pad used for any given test only after the clinical exposure and subsequent analysis of the clinical effect. This process is called "unblinding", and is used in double-blind studies, which are considered the highest level of clinical testing.

The modified pad 25 as shown in FIG. 7 also permits the creation of different ultrasound energy deposition patterns, beam shapes, etc., depending upon the geometry of the foam disk 105 and the aperture 110. This allows different exposure conditions without the need to make different ultrasound transducers, which are much more expensive to construct than the gel pads. The modified pad 25 may be used for experiments other than neuromodulation, experiments which do not involve blinding, and experiments such as animal exposure, cell exposures, tissue exposure, beam scanning experiments, and the creation of novel ultrasound beams for other purposes that are not easily achievable by transducer modification.

While all of the invention has been illustrated by a description of various embodiments and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. A structure for use with an ultrasound transducer configured to emit ultrasound energy, the structure comprising:
   a first outer casing comprising a first material, the first material having a first acoustic attenuation that permits transmission of the ultrasound energy from the ultrasound transducer through the first outer casing; and
   a disk positioned inside the first outer casing, the disk comprising a second material that differs in composition from the first material, and the second material having a second acoustic attenuation greater than the first acoustic attenuation of the first material such that the disk blocks substantially all of the ultrasound energy emitted by the ultrasound transducer from being transmitted through the disk,
   wherein the first outer casing has an exterior surface, the first material fully surrounds the disk, the disk is surrounded by a gap between the disk and the exterior surface of the first outer casing, and the first material is either opaque or translucent to an extent sufficient to prevent visualization of the disk through the first outer casing.

2. The structure of claim 1 wherein the second material is an open-cell foam.

3. The structure of claim 1 wherein the second material is a closed-cell foam.

4. The structure of claim 1 wherein the disk is centrally located inside the first outer casing.

5. The structure of claim 1 wherein the gap is an annular gap.

6. The structure of claim 1 wherein the first outer casing is configured to be disposed between the ultrasound transducer and a brain of a patient.

7. The structure of claim 6 wherein the ultrasound transducer is configured to emit the ultrasound energy toward the brain of the patient, and the disk is configured to block transmission of substantially all of the ultrasound energy from the ultrasound transducer to the brain of the patient.

8. The structure of claim 6 further comprising:
   a mating ring configured to mate the first outer casing with a face of the ultrasound transducer.

9. The structure of claim 1 further comprising:
   a second outer casing comprising the first material,
   wherein the second outer casing does not surround a disk comprised of the second material.

10. A structure for use with an ultrasound transducer configured to emit ultrasound energy, the structure comprising:
    an outer casing comprising a first material, the first material having a first acoustic attenuation that permits transmission of the ultrasound energy from the ultrasound transducer through the outer casing; and
    a disk positioned inside the outer casing, the disk comprising a second material that differs in composition from the first material, and the second material having a second acoustic attenuation greater than the first acoustic attenuation of the first material such that the disk blocks substantially all of the ultrasound energy emitted by the ultrasound transducer from being transmitted through the disk,
    wherein the first material fully surrounds the disk, the first material is either opaque or translucent to an extent sufficient to prevent visualization of the disk through the outer casing, and the outer casing has a plurality of exterior surfaces in an angled relationship to define a wedge shape.

11. The structure of claim 10 wherein the outer casing is configured to be disposed between an external ultrasound transducer and a brain of a patient, and the wedge shape of the outer casing provides a wedge angle that angles the external ultrasound transducer relative to an anatomical region within the brain.

12. A structure for use with an ultrasound transducer configured to emit ultrasound energy, the structure comprising:
- an outer casing comprising a first material, the first material having a first acoustic attenuation that permits transmission of the ultrasound energy from the ultrasound transducer through the outer casing; and
- a disk positioned inside the outer casing, the disk comprising a second material that differs in composition from the first material, and the second material having a second acoustic attenuation greater than the first acoustic attenuation of the first material such that the disk blocks substantially all of the ultrasound energy emitted by the ultrasound transducer from being transmitted through the disk,
- wherein the first material fully surrounds the disk, the first material is either opaque or translucent to an extent sufficient to prevent visualization of the disk through the outer casing, the outer casing has a first diameter, and the disk has a second diameter that is less than the first diameter.

13. The structure of claim 12 wherein the disk is centrally imbedded located in the outer casing.

14. A structure for use with an ultrasound transducer configured to emit ultrasound energy, the structure comprising:
- an outer casing comprising a first material, the first material having a first acoustic attenuation that permits transmission of the ultrasound energy from the ultrasound transducer through the outer casing; and
- a disk positioned inside the outer casing, the disk comprising a second material that differs in composition from the first material, and the second material having a second acoustic attenuation greater than the first acoustic attenuation of the first material such that the disk blocks substantially all of the ultrasound energy emitted by the ultrasound transducer from being transmitted through the disk,
- wherein the first material fully surrounds the disk, the first material is either opaque or translucent to an extent sufficient to prevent visualization of the disk through the outer casing, and the disk includes an aperture.

15. The structure of claim 14 wherein the aperture is circular.

16. The structure of claim 14 wherein the aperture is non-circular.

17. The structure of claim 14 wherein the outer casing is configured to be disposed between an external ultrasound transducer and a brain of a patient.

18. The structure of claim 17 wherein the external ultrasound transducer is configured to emit the ultrasound energy toward the brain of the patient, and the disk is configured to partially transmit the ultrasound energy from the external ultrasound transducer to the brain of the patient.

* * * * *

UNITED STATES PATENT AND TRADEMARK OFFICE
CERTIFICATE OF CORRECTION

| | | |
|---|---|---|
| PATENT NO. | : 12,201,856 B2 | Page 1 of 1 |
| APPLICATION NO. | : 17/680466 | |
| DATED | : January 21, 2025 | |
| INVENTOR(S) | : Samantha F. Schafer and Mark E. Schafer | |

It is certified that error appears in the above-identified patent and that said Letters Patent is hereby corrected as shown below:

In the Claims

Column 11, Claim 13, Line 23 reads:
"imbedded located in the outer casing."
It should read:
-- located in the outer casing. --

Signed and Sealed this
Eighteenth Day of February, 2025

Coke Morgan Stewart
*Acting Director of the United States Patent and Trademark Office*